US008603769B2

(12) United States Patent
Feng et al.

(10) Patent No.: US 8,603,769 B2
(45) Date of Patent: Dec. 10, 2013

(54) METHOD FOR DIRECT AND RAPID IDENTIFICATION OF MICROORGANISMS AND ANTIMICROBIAL SUSCEPTIBILITY TESTING FROM POSITIVE BLOOD CULTURES

(71) Applicant: Becton, Dickinson and Company, Franklin Lakes, NJ (US)

(72) Inventors: Liping Feng, Cockeysville, MD (US); William B. Brasso, Columbia, MD (US); Song Shi, Reisterstown, MD (US); Ben Turng, Ellicott City, MD (US); Susan M. Kircher, Hanover, PA (US); Vanda White, Baltimore, MD (US); Dyan Luper, Cockeysville, MD (US); Julie Rosales, Randallstown, MD (US); Gretta Campbell, Glen Rock, PA (US); Adrien Malick, Granite, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/647,072

(22) Filed: Oct. 8, 2012

(65) Prior Publication Data

US 2013/0089886 A1    Apr. 11, 2013

Related U.S. Application Data

(60) Provisional application No. 61/544,407, filed on Oct. 7, 2011.

(51) Int. Cl.
*C12Q 1/04* (2006.01)
*C12Q 1/24* (2006.01)

(52) U.S. Cl.
USPC .............................. 435/30; 435/252.4; 435/34

(58) Field of Classification Search
None
See application file for complete search history.

(56) References Cited

U.S. PATENT DOCUMENTS

| | | | |
|---|---|---|---|
| 5,922,593 A | 7/1999 | Livingston | |
| 6,096,272 A | 8/2000 | Clark et al. | |
| 6,372,485 B1 | 4/2002 | Clark et al. | |
| 6,849,422 B1 | 2/2005 | Wiles et al. | |
| 7,115,384 B2 | 10/2006 | Clark et al. | |
| 7,425,327 B2 * | 9/2008 | Masure et al. | 424/130.1 |
| 8,252,546 B2 * | 8/2012 | Briles et al. | 435/7.34 |

FOREIGN PATENT DOCUMENTS

| | | |
|---|---|---|
| WO | WO2008/084409 A2 * | 7/2008 |
| WO | 2010100612 A1 | 9/2010 |

OTHER PUBLICATIONS

Sigma-Aldrich, Inc., Product Information Sheet, Mutanolysin, Product No. M9901, Sep. 2007.*

"The case for accelerated susceptibility testing in the Era of Antibiotic resistance", A White Paper by MicroPhage, Inc., Mar. 30, 2011.

Baker et al.,, "Action of synthetic detergents on the metabolism of bacteria", Oct. 14, 1940.

Bruins et al., "Identification and susceptibility testing of enterobacteriaceae and *Pseudomonas aeruginosa* by Direct Inoculation from Positive BACTEC Blood Culture Bottles into Vitek 2", Journal of Clinical Microbiology, Jan. 2004, vol. 42, No. 1, p. 7-11.

Chapin et al "Direct susceptibility testing of positive blood cultures by using sensititre broth microdilution plates", Journal of Clinical Microbiology, Oct. 2003, p. 4751-4754.

Drancourt, "Detection of microorganisms in blood specimens using matrix-assisted laser desorption ionization time-of-flight mass spectrometry: a review", Clin Microbiol Infect, Jun. 8, 2010, 16: 1620-1625.

Elder et al., "Verification and validation of procedures in the clinical microbiology laboratory", Feb. 1997, Cumulative Techniques and Procedures in Clinical Microbiology, No. 31.

Ferroni et al., "Real-Time identification of bacteria and *Candida* species in positive blood culture broths by Matrix-Assisted laser desorption ionozation-time of flight mass spectrometry", Journal of Clinical Microbiology, May 2010, vol. 48, No. 5, p. 1542-1548.

Funke et al., "Use of the BD PHOENIX automated microbiology system for direct identification and susceptibility testing of Gram-Negative rods from positive blood cultures in a Three-Phase trial", Journal of Clinical Microbiology, Apr. 2004, vol. 42, No. 4, p. 1466-1470.

Giudicelli et al., "Attachment of pneumococcal autolysin to wall teichoic acids, an essential step in enzymatic wall degradation", Journal of Bacteriology, 1984, 158(3):1188.

Lehtonen, Olli-Pekka J., "Inhibition of pneumococca; autolysis in Lysis-Centrifugation Blood Culture", Journal of Clinical Microbiology, Sep. 1986, vol. 24, No. 3, p. 493-494.

Ling et al., "Evaluation of VITEK 2 rapid identification and susceptibility testing system against Gram-Negative Clinical Isolates", Journal of Clinical Microbiology, Aug. 2001, vol. 39, No. 8, p. 2964-2966.

Lupetti et al., "Rapid identification and antimicrobial susceptibiliity profiling of Gram-positive cocci in blood cultures with the Vitek 2 system", Eur J Clin Microbiol Infect Dis (2010) 29:89-95.

Prod'hom et al., "Matrix-assisted laser desorption ionization-time of flight mass spectrometry for direct bacterial identification from positive blood culture pellets", Journal of Clinical Microbiology, Apr. 2010, vol. 48, No. 4, p. 1481-1483.

(Continued)

*Primary Examiner* — John S Brusca
*Assistant Examiner* — Sharon M Papciak
(74) *Attorney, Agent, or Firm* — Lerner, David, Littenberg, Krumholz & Mentlik, LLP

(57) ABSTRACT

Methods of the invention include the isolation of intact, viable microorganism(s) from positive blood culture ("PBC") samples for use in downstream analyses such as identification and antimicrobial susceptibility testing ("AST"). The methods involve collecting a portion of the PBC sample, adding a choline-containing solution, lysing the blood cells, isolating the viable microorganism, and performing downstream analysis of the isolated, viable microorganism. The methods can be applied to a variety of gram-positive bacteria, gram-negative bacteria, and/or yeast, and particularly to strains of *S. pneumoniae*.

31 Claims, 2 Drawing Sheets

(56) References Cited

OTHER PUBLICATIONS

Hansson, "Microfluidic blood sample preparation for rapid sepsis diagnostics", KTH Engineering Sciences, 2012.
Stevenson et al., "Rapid identification of bacteria in positive blood culture broths by matrix-assisted laser desorption ionization-time of flight mass spectrometry", Journal of Clinical Microbiology, Feb. 2010, vol. 48, No. 2, p. 444-447.
Bhakdi et al., "Mechanism of membrane damage by streptolysin-O", Infection and Immunity, Jan. 1985, vol. 47, No. 1, p. 52-60.
Petti et al., "*Streptococcus pneumoniae* antigen test using positive blood culture bottles as an alternative method to diagnose pneumococcal bacteremia", Jounral of Clinical Microbiology, May 2005, vol. 43, No. 5, p. 2510-2512.
Howden R., "Use of anaerobic culture for the improved isolation of *Streptococcus pneumoniae*", J. Clin. Path., 1976, 29, 50-53.
Zierdt, charles H., "Simplified lysed-blood culture technique", Journal of Clinical Microbiology, Mar. 1986, vol. 23, No. 3, p. 452-455.

* cited by examiner

METHOD FOR DIRECT AND RAPID IDENTIFICATION OF MICROORGANISMS AND ANTIMICROBIAL SUSCEPTIBILITY TESTING FROM POSITIVE BLOOD CULTURES

CROSS-REFERENCE TO RELATED APPLICATIONS

This application claims the benefit of the filing date of U.S. Provisional Patent Application No. 61/544,407 filed Oct. 7, 2011, the disclosure of which is hereby incorporated herein by reference.

BACKGROUND OF THE INVENTION

Sepsis is a serious medical condition caused by an overwhelming response of the host immune system to infection. It can trigger widespread inflammation, which can give rise to impaired blood flow. As sepsis progresses, the body's organs can be starved for oxygen and nutrients, causing permanent damage and eventual failure. Left improperly diagnosed or otherwise untreated, the heart may weaken and septic shock can occur, leading to multiple organ failure and death. Blood cultures are required to detect the presence of bacteria or yeast in the blood of sepsis patients, to identify the microorganism(s) present, identify antibiotic susceptibilities, and guide treatment. Positive blood cultures ("PBC") are used to identify the microorganism(s) and perform antimicrobial susceptibility testing ("AST"). In order to identify the microorganism(s) and perform susceptibility testing, intact, viable microorganism(s) need(s) to be isolated from the blood cells and other debris in the collected sample.

Current techniques for isolating viable microorganism(s) from a PBC sample often utilize liquid separation methods containing lysis buffers with detergents that lyse the blood cells in the PBC sample. After lysis, the lysed blood cells can be removed while the viable microorganism(s) is/are retained. However, the use of these lysis buffers often result in non-viable microorganism(s) which is/are insufficient for performing certain biochemical testing such as AST testing. This is particularly true for *Streptococcus pneumoniae* (*S. pneumoniae*), which is often difficult to isolate and identify. Ultimately, time consuming methods, such as sub-culturing of the microorganism(s), are required in order to obtain a plated pure culture of viable microorganism(s). Preparation of a plated pure culture can take up to 48 hours which may result in many of the septicemia patients being initially treated with inappropriate antibiotics.

Accordingly, it is desirable to develop methods that rapidly separate microorganism(s) from a PBC sample while maintaining the viability of the microorganism(s), so that analytical methods that require cell viability, such as AST testing, can be performed. Additionally, it is desirable that these methods do not contain any substances which would interfere with methods of identifying the microorganism(s), for example mass spectrometry. Ideally, the desired methods would allow for the rapid isolation of viable microorganism(s) from a single PBC sample that can be used for multiple down-stream analysis, such as, both identification by mass spectrometry and AST testing. In addition, the methods should be able to identify a wide panel of microorganisms, including the most difficult of organisms to identify, for example *S. pneumoniae*.

BRIEF SUMMARY OF THE INVENTION

Various embodiments described herein enable the rapid isolation of viable microorganism(s) from a positive blood culture sample (PBC). The methods include treating a PBC sample with a choline-containing solution and a lysis buffer known to lyse blood cells. The methods of various embodiments allow for the isolation of viable microorganism(s) from a single PBC sample followed by one or multiple downstream tests such as identification of the microorganism(s) and AST testing.

In one embodiment, a method for preparing a PBC sample includes obtaining a biological sample determined to contain at least one microorganism, combining at least a portion of the biological sample with a choline-containing solution and a lysis buffer to lyse the blood cells, isolating the viable microorganism(s), optionally preparing a plated pure culture or a single inoculum from the isolated microorganism(s), and performing downstream analysis on the isolated, viable microorganism(s) or optional plated pure culture/inoculum.

In yet another embodiment, the methods described herein are used to isolate and perform downstream analysis on gram-positive bacteria, gram-negative bacteria, or yeast. In another embodiment, the gram-positive bacteria include *S. pneumoniae* as well as other species of Streptococci.

DETAILED DESCRIPTION

Embodiments described herein provide for methods of isolating viable microorganism(s) from a PBC sample and subsequent downstream testing of the isolated microorganism(s). The various methods allow for multiple downstream analyses of microorganism(s) isolated from a common PBC sample.

In one embodiment, a method for isolating/detecting/evaluating viable microorganism(s) from a PBC includes obtaining a biological sample determined to contain at least one microorganism, combining at least a portion of the biological sample with a choline-containing solution and a lysis buffer to lyse the non-target cells (e.g. blood cells in a blood sample) in the biological sample, isolating the intact microorganism(s), optionally preparing a plated pure culture or a single inoculum, and performing downstream analysis on the isolated, viable microorganism(s) or optional plated pure culture/inoculum.

Figure 1:
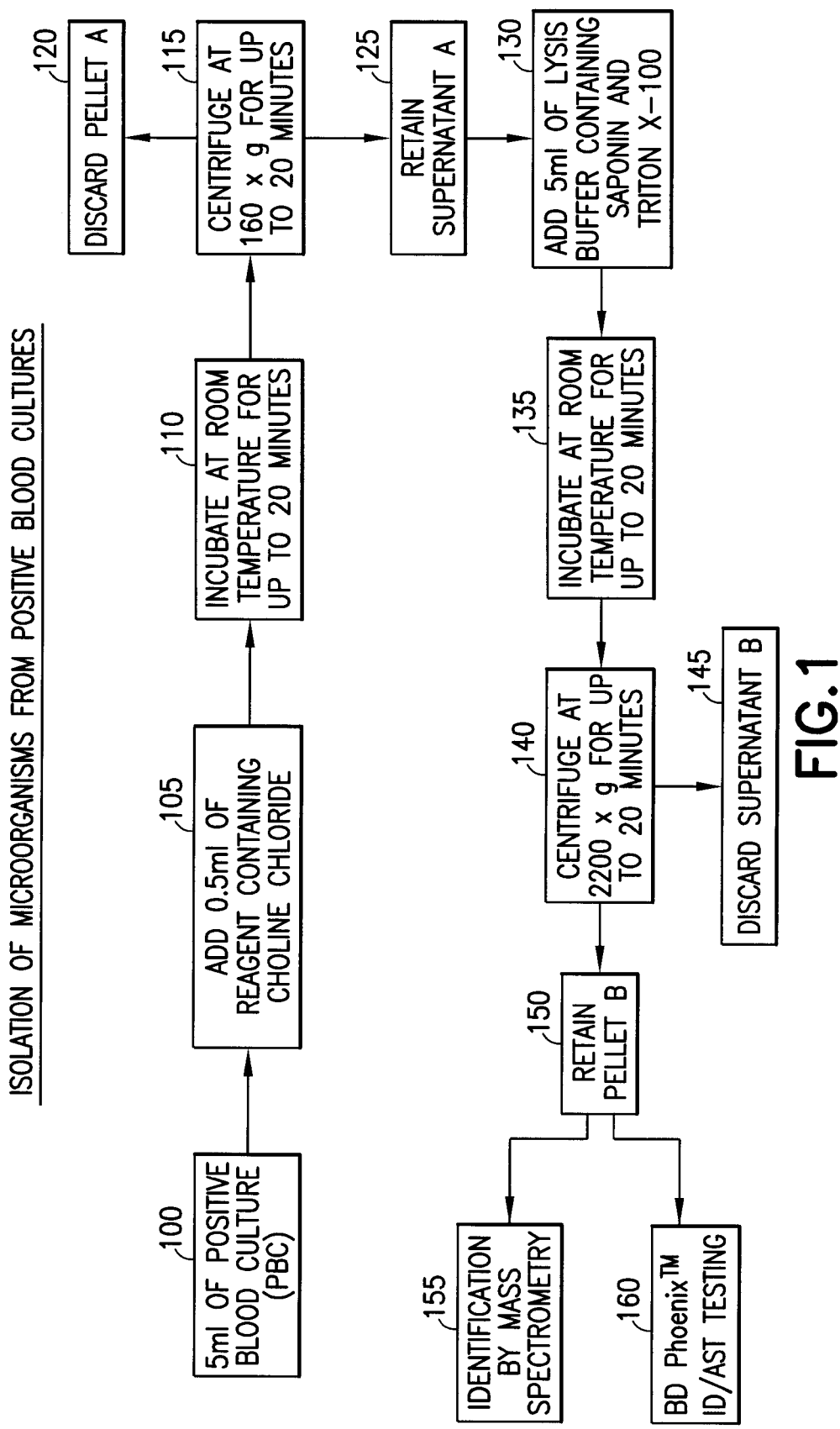
FIG. 1 illustrates the method of one embodiment described herein for isolating viable microorganism(s) from a single PBC sample with two centrifugation steps and subsequent identification of the microorganism(s) and AST testing.

FIG. 1 illustrates one method of the various embodiments described herein. A portion of a PBC sample (e.g., 5 ml) 100 is obtained. A reagent (e.g., 0.5 ml) 105 containing an aqueous solution of choline chloride is added to PBC sample 100 at a final concentration of choline when added to PBC sample 100 of about 1.8% by volume. The mixture of PBC sample 100 and reagent containing choline chloride 105 is incubated (step 110) at room temperature for up to about 20 minutes. The incubated mixture (step 110) is centrifuged (step 115) at about 160×g for up to about 20 minutes. The resulting pellet A 120, containing most of the blood cells, is discarded, while supernatant A 125, containing viable microorganism, is retained. A lysis buffer (e.g., 5 ml) 130 containing saponin and Triton X-100 is added to supernatant A 125 at a final concentration of saponin and Triton X-100 when added to supernatant A 125 at about 0.117% by volume and about 0.335% by volume, respectively. The mixture of supernatant A 125 and lysis buffer 130 is incubated (step 135) at room temperature for up to about 20 minutes to lyse any residual blood cells. The incubated sample (step 135) is centrifuged (step 140) at about 2200×g for up to about 20 minutes to produce supernatant B 145 and pellet B 150. Supernatant B 145, containing the lysed blood cells, is discarded, while pellet B 150, containing isolated/viable microorganism, is retained for identification by mass spectrometry 155 and/or preparation for BD Phoenix™ ID/AST testing 160.

A positive blood culture (PBC) sample may be obtained by methods known to those skilled in the art and is not described in detail herein. The PBC sample may include samples determined to be positive for at least one microorganism by detection with, for example, the BD BACTEC™ Instrumented Blood Culture System (Becton, Dickinson and Company). In one embodiment the microorganism(s) includes gram-positive bacteria, gram-negative bacteria, or yeast. In another embodiment, the microorganism(s) is the gram-positive bacterium *S. pneumoniae*. The starting volume of the PBC sample is not limited to any particular maximum or minimum volume.

There is no limit to the type of choline in the choline-containing solution that can be used in the various methods described herein. Choline is a quarternary ammonium salt containing the N,N,N-trimethylethanolammonium cation and is represented by the general formula:

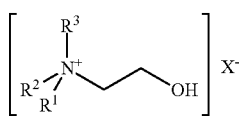

Formula 1 wherein $R^1$, $R^2$, and $R^3$ independently represent a saturated or unsaturated hydrocarbon group and/or aromatic group, and X represents a negative charged group such as chloride, fluoride, nitrate, bicarbonate etc. In one embodiment, the choline-containing solution comprises choline chloride. In another embodiment, the choline-containing solution comprises phosphorylcholine.

Without being bound by a particular theory, it is believed that the choline-containing solution inhibits, prevents, and/or mitigates autolysis of the microorganism, particularly *S. pneumonia* in the presence of lysis buffer. While applicants do not wish to be held to a particular theory, the presence of choline may block the hydrolytic activity of the autolytic enzyme N-acetylmuramic acid-L-alanine amidase. This enzyme, if active, may break down or destroy microorganism(s) in the sample. In addition, the choline-containing solution may also mitigate lysis of the microorganism(s) caused by the detergents used to lyse the blood cells in a PBC sample. Therefore, the use of choline in sample preparation methods that utilize lysis buffers allows for the rapid and successful isolation of a wider array of viable microorganisms, including *S. pneumoniae*, without the need for sub-culturing.

The choline-containing solution can be prepared with the choline and suitable diluents known to those skilled in the art, such as water, buffers, and combinations thereof, etc. In one embodiment the choline-containing solution is an aqueous solution of choline. The concentration of choline in the choline-containing solution is not limited and the choline concentration for a particular application is readily chosen by the skilled person. In one embodiment, the concentration of choline in the choline-containing solution is up to about 20% by volume.

There is no limit to the final concentration of choline when combined with the sample. In one embodiment, the final concentration of choline when combined with the sample is greater than or equal to about 0.25% by volume, preferably greater than or equal to about 1% by volume. In another embodiment the final concentration of choline when combined with the sample is in the range of about 0.25% by volume to about 10% by volume, preferably about 1% by volume to about 5% by volume. In another embodiment, the final concentration of choline when combined with the sample is 1.8% by volume. In yet another embodiment the final concentration of choline when combined with the sample is 4% by volume. Again, the concentration of choline in combination with the sample in the context of a particular application is readily determined by the skilled person.

One skilled in the art is aware of various lysis buffers that can be used with the methods described herein to lyse blood cells. Various detergents can be included in the lysis buffer and can be combined with the PBC sample to lyse the blood cells while maintaining viability of the microorganism(s). For example, in one embodiment, the lysis buffer comprises at least one non-ionic detergent. In an alternative embodiment, the lysis buffer comprises octyl-B-D-glucopyranoside ("OG"), triton X-100, saponin, or combinations thereof. In another alternative embodiment, the non-ionic detergent(s) is/are able to lyse the blood cells but does/do not interfere with downstream analysis, for example, identification by mass spectrometry. Examples of such detergents include, but are not limited to, OG, n-nonyl β-D-glucoside (NG), octanoyl-N-methylglucamide, nonanoyl-N-methylglucamide, decanoyl-N-methylglucamide, n-dodecyl-β-D-maltoside, and n-octyl-rac-2,3-dioxypropylsulfoxide.

The final concentration of the detergent(s) when combined with the sample is not limited so long as the detergent(s) are used at a concentration that will hemolyze (or otherwise break down) at least a portion of the blood cells, while leaving at least a portion of the microorganism(s) in the sample intact and viable.

Other constituents that may be included in the lysis buffer are known to those skilled in the art and are not disclosed in detail herein. These other constituents may include, for example, water, buffers, broths, additional detergents, etc.

Various methods are contemplated for combining the biological sample with the choline-containing solution and lysis buffer. The biological sample can be combined with a choline-containing solution any time prior to and or simultaneous with the addition of the lysis buffer. In one embodiment, the sample is combined with a choline-containing solution and lysis buffer simultaneously. In yet another embodiment, the choline-containing solution is added after the sample has been determined to contain at least one microorganism but prior to the addition of lysis buffer.

In one embodiment, a method for preparing a PBC sample includes: i) obtaining a biological sample determined to contain at least one microorganism; ii) incubating at least a portion of the biological sample with a choline-containing solution for a period of time; iii) adding a lysis buffer to the biological sample containing the choline-containing solution to lyse the blood cells and incubating the mixture for a period of time; iv) isolating the viable microorganism(s); v) optionally, preparing a plated pure culture or an inoculum from the isolated microorganism(s); and vi) performing downstream analysis on the isolated microorganism(s) or optional plated pure culture/inoculum. In one embodiment, each of the incubation steps is performed for up to about 20 minutes at room temperature.

In another embodiment, a method for preparing a PBC sample includes: i) obtaining a biological sample determined to contain at least one microorganism; ii) incubating at least a portion of the biological sample with a choline-containing solution for a period of time; iii) centrifuging the biological sample containing the choline-containing solution at a low speed to pellet the majority of the blood cells (e.g. at a speed in the range of about 500×g or less); iv) retaining the supernatant containing viable microorganism(s) while discarding the pelleted blood cells; v) adding a lysis buffer to the supernatant to lyse any remaining blood cells and incubating the mixture for a period of time; vi) isolating the viable microorganism(s) by centrifuging the mixture of lysis buffer and microorganism at a high speed to pellet the viable microorganism(s) (e.g. at a speed in the range of about 500×g up to the tolerance of the centrifuge container); vii) discarding the supernatant containing debris and retaining the pellet containing viable microorganism(s); viii) optionally, preparing a plated pure culture or an inoculum from the isolated microorganism; and ix) performing downstream analysis on the isolated, viable microorganism(s). In one embodiment, each of the incubation steps is performed for up to about 20 minutes at room temperature.

In yet another embodiment, a method for preparing a PBC sample includes: i) obtaining a biological sample determined to contain at least one microorganism; ii) incubating at least a portion of the biological sample with both a choline-containing solution and a lysis buffer simultaneously for a period of time; iii) isolating the viable microorganism(s) by centrifuging the mixture of lysis buffer and microorganism(s) at a high speed to pellet the viable microorganism(s) (e.g. at a speed in the range of about 500×g up to the tolerance of the centrifuge container); vii) discarding the supernatant containing debris and retaining the pellet containing viable microorganism(s); viii) optionally, preparing a pure culture or an inoculum from the isolated microorganism(s); and ix) performing downstream analysis on the isolated microorganism(s) or optional plated pure culture/inoculum. In one embodiment, each of the incubation steps is performed for up to about 20 minutes at room temperature.

Figure 2:
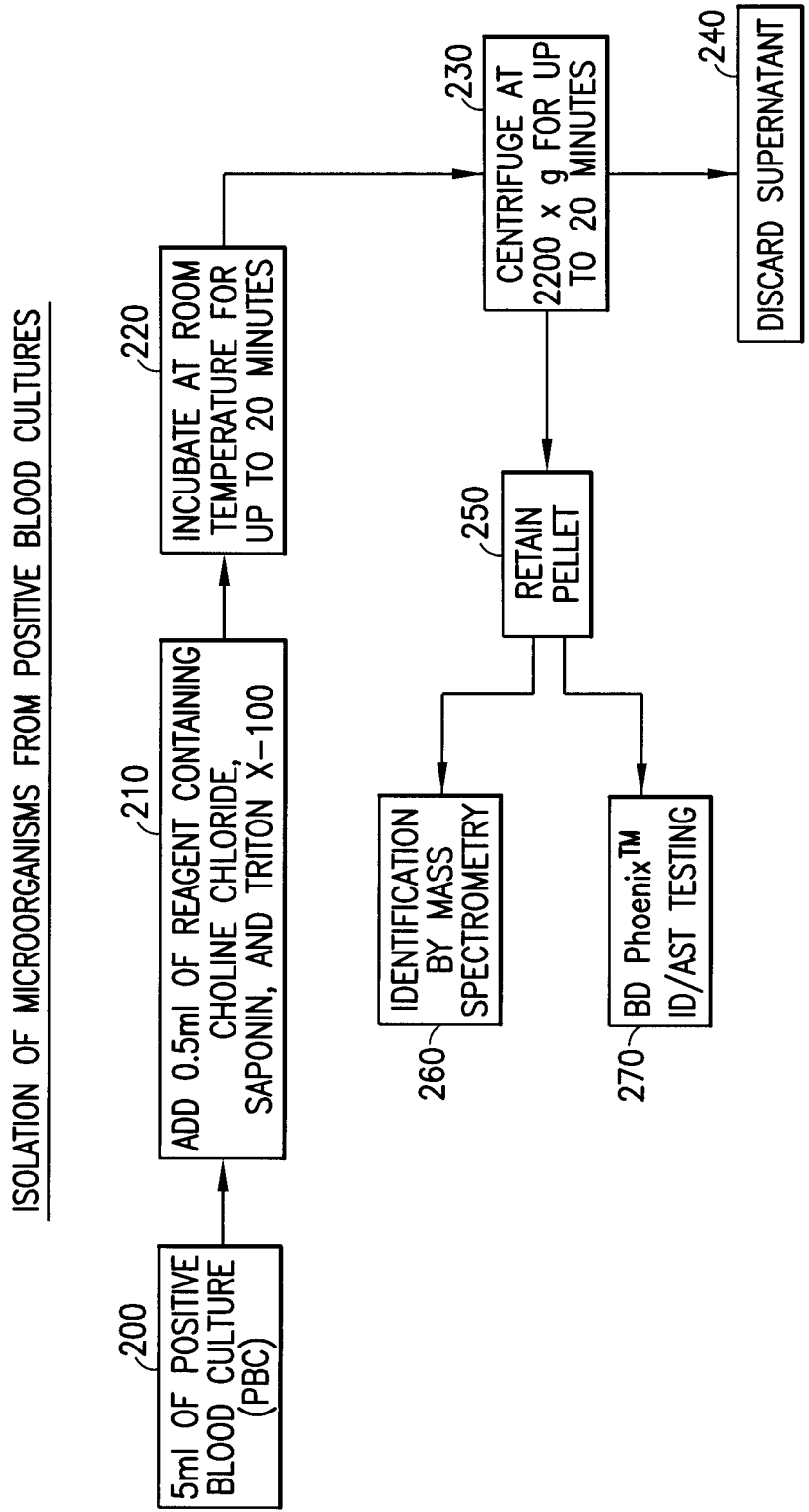
FIG. 2 illustrates the method of one embodiment described herein for isolating viable microorganism(s) from a single PBC sample with one centrifugation step and subsequent identification of the microorganism(s) and AST testing.

FIG. 2 illustrates one method of the various embodiments described herein. A portion of a PBC sample (5 ml) 200 is obtained. A reagent (e.g., 0.5 ml) 210 containing an aqueous solution of choline chloride, saponin, and Triton X-100 is added to PBC sample 200 at final concentrations of choline, saponin, and Triton X-100 when added to PBC sample 200 of about 1.8% by volume, about 0.117% by volume, and about 0.335% by volume, respectively. The mixture of PBC sample 200 and reagent 210 is incubated (step 220) at room temperature for up to about minutes. The incubated sample (step 220) is centrifuged (step 230) at about 2200×g for up to about 20 minutes to produce supernatant 240 and pellet 250. Supernatant 240 is discarded, while pellet 250, containing isolated/viable microorganism(s), is retained for identification by mass spectrometry 260 and/or preparation for BD Phoenix™ ID/AST testing 270.

In one embodiment, the isolated microorganism(s) is processed in preparation for downstream testing. This includes, for example, resuspending at least a portion of the isolated microorganism(s) in a fluid, for example, water, OG, BD Phoenix™ ID broth, or a non-ionic detergent. In one embodiment, the isolated microorganism is prepared for identification by mass spectrometry by resuspending the isolated microbial pellet in a solution and depositing a portion of the resuspended pellet onto a MALDI-TOF MS plate, or by directly depositing a portion of the isolated microbial pellet onto a MALDI-TOF MS plate without first resuspending the pellet in a solution. In another embodiment, the isolated microbial pellet is prepared for BD Phoenix™ ID/AST testing by resuspending the isolated microbial pellet in a solution and adjusting the suspension to a specific concentration of about 0.5 McFarland Standard. Additional methods for preparing the isolated microorganism(s) for downstream analysis are contemplated, known to those skilled in the art, and are not described in detail herein.

The isolated microorganism(s) can be used for multiple downstream analyses, including identification of the microorganism(s) (e.g. mass spectrometry, phenotypical, or molecular identification methods, etc.) and AST testing. The AST methods may be applicable to most manual and automated AST systems known in the art, including BD Phoenix™ ID/AST, disk diffusion (Sensi-Disc), agar dilution, and micro-/macrotube dilution methods. Identification methods and AST testing are well known to one skilled in the art and is not described in detail herein. Additional downstream testing can also include, for example, different phenotypic identification systems or methods utilizing enzymatic, biochemical reactions, different molecular or phenotypic identification systems, and/or growth based identification schemes. They may also be used to detect resistance markers that confer protection of the bacterial isolate from certain antimicrobial agents and classes.

In one embodiment, the various methods described herein can further include preparation of a plated pure culture or a single inoculum from the isolated microorganism(s). Methods for the preparation of a plated pure culture or inoculum are known to those skilled in the art and not described in detail herein. The plated pure culture or inoculum can be prepared to obtain adequate amount of sample should additional downstream testing be required.

EXAMPLES

Example 1

Isolation of Viable Microorganism from a PBC Sample and Subsequent Identification by Mass Spectrometry Twenty different PBC samples known to each contain a different strain of a gram-positive bacterium were prepared according to the method below. The twenty different microbial strains tested are listed in Table 1 below.

TABLE 1

Gram-positive strains tested

| Gram-positive Microorganism | Number of Strains |
|---|---|
| *Enterococcus faecalis* | 4 |
| *Staphylococcus aureus* | 4 |
| *Staphylococcus epidermidis* | 2 |
| *Staphylococcus haemolyticus* | 1 |
| *Staphylococcus lugunensis* | 1 |
| *Streptococcus agalactiae* | 2 |
| *Streptococcus pneumoniae* | 3 |
| *Streptococcus pyogenes* | 1 |
| *Viridans Streptococci* | 2 |
| Total Number of Strains Tested | 20 |

Three of the twenty strains contained S. pneumoniae. A portion of each PBC sample (5 ml) was combined with 0.5 ml of a 20% aqueous solution by volume of choline chloride and incubated at room temperature for 20 minutes. The final concentration of choline chloride, when combined with the sample, was 1.8% by volume. The PBC sample containing the choline chloride solution was centrifuged at 160×g for 5 minutes to pellet most of the blood cells, leaving the viable microorganism in the supernatant. The supernatant was transferred to a 15 ml conical tube. Lysis buffer containing 4.5 ml of lytic broth (BD BACTEC™ Lytic/10 Anaerobic/F Medium Catalog #442265) and 0.5 ml of 100 mM Triton X-100 was added to the supernatant and incubated at room temperature for 5 minutes. The mixture was centrifuged at 2200×g at room temperature for 10 minutes. The supernatant, containing debris, was discarded, while the pellet, containing viable microorganism, was retained for identification by mass spectrometry.

A portion of the pelleted microorganism was resuspended in 600 μl water or 2 mM OG in a microcentrifuge tube. The turbidity was visually adjusted to >0.5 McFarland Standard. A portion of the sample (1-1.5 μl) was spotted onto a MALDI-MS plate and allowed to air dry. Formic acid (1-2 μl of a 70% aqueous solution) was overlaid onto the dried, spotted sample and allowed to air dry. The dried sample was overlaid with 1 μl of MALDI-MS matrix solution (MALDI-MS matrix solution prepared by dissolving 2.5 mg of HCCA in 250 μl of 2.5% trifluoroacetic acid and 47.5% acetonitrile in de-ionized water) and allowed to air dry before identification by MALDI-TOF mass spectrometry. All mass spectrometry data was recorded on a Bruker Microflex LT with Biotyper 2.0 software. The methods of preparing the isolated microbial pellet and identifying the microorganism by the mass spectrometry are further described in U.S. application Ser. No. 13/636,944, filed Aug. 31, 2012, and incorporated herein by reference.

For comparison, sample was also prepared using a prior art method (Bruker Sepsityper™ Kit Catalog #270170). A portion of a PBC sample (1 ml) was placed in a 2.0 ml microcentrifuge tube. Lysis buffer (200 μl) was added to the microcentrifuge tube containing the PBC sample. The mixture was vortexed for approximately 10 seconds followed by centrifugation for 1 minute at 2200×g. The supernatant was removed by pipetting and discarded. The pellet, containing isolated microorganism, was resuspended in 1 ml of the washing buffer and centrifuged for 1 minute at 3000×g. The supernatant was removed by pipetting and discarded. Water (300 μL) was added to the microcentrifuge tube and vortexed thoroughly. After vortexing, 900 μL of ethanol was added to the mixture and vortexed again. The mixture was centrifuged at maximum speed for 2 minutes, the ethanol decanted, and the remaining mixture was centrifuged again for two minutes. All excess ethanol was removed with a pipette. Formic acid (50 μL of a 70% solution) was added to the pellet containing intact microorganism and the mixture was vortexed thoroughly. Acetonitrile (50 μL of a 100% solution) was added to the mixture and vortexed thoroughly. The mixture was centrifuged at maximum speed for 2 minutes. A portion of the supernatant (1 μL) was spotted onto a MALDI-MS plate and allowed to air dry. The dried sample was overlaid with 1 μL of MALDI matrix solution (MALDI matrix solution prepared by dissolving 2.5 mg of HCCA in 250 μl of 2.5% trifluoroacetic acid and 47.5% acetonitrile in de-ionized water) and allowed to air dry before identification by MALDI-MS. All mass spectrometry data was recorded on a Bruker Microflex LT with Biotyper 2.0 software.

The prior art methods resulted in 16/20 correct identifications for the gram-positive panel, including 0/3 correct identifications of the S. pneumoniae strains. On the other hand, the methods described herein were able to correctly identify 19/20 strains for the gram-positive panel, including 2/3 S. pneumoniae strains. The results were identical whether the pelleted microorganism was resuspended in 600 μl water or 2 mM OG. These results indicate that the methods described herein invention can be used to isolate and identify viable microorganism(s) from a PBC sample for a wider variety of strains of microorganism(s), including those strains often difficult to identify such as S. pneumoniae, than the prior art methods.

Example 2

Isolation of Viable Microorganism from a PBC Sample Using Two Different Lysis Buffers and Subsequent Identification by BD Phoenix™ ID A gram-positive panel and a gram-negative panel of PBC samples were generated using the BD BACTEC™ Instrumented Blood Culture System (Becton, Dickinson and Company) with each test organism, placing the sealed culture bottles in a BD BACTEC™ FX Automated Blood Culture Instrument (Becton, Dickinson and Company), and incubating the bottle until a positive result was indicated, usually within 12-24 hours. A portion of each PBC sample (5 ml) was added to 0.5 ml of a 20% aqueous solution by volume of choline chloride and incubated at room temperature for 20 minutes. The final concentration of choline chloride when combined with the sample was 1.8% by volume. The PBC sample containing the choline chloride solution was centrifuged at 160×g for 5 minutes to pellet the blood cells, leaving the microorganism in the supernatant. The supernatant was transferred to another tube. One of two different lysis buffers was added to the supernatant and incubated at room temperature for 5 minutes. Lysis buffer #1 contained lytic broth, saponin, and Triton X-100. The final concentration of saponin and Triton X-100 when combined with the sample was 0.117% by volume and 0.335% by volume, respectively. Lysis buffer #2 contained OG and saponin. The final concentration of OG and saponin when combined with the sample was 0.25% by volume and 0.125% by volume respectively. The mixture was centrifuged at 2200×g at room temperature for 10 minutes. The supernatant was discarded while the pellet, containing viable microorganism, was retained for identification by the BD Phoenix™ Identification System. A remaining portion of the pellet was retained for AST testing as described in Example 3 below.

The portion of the inoculum used for identification was poured into the identification portion of a BD Phoenix™ ID/AST panel (Becton, Dickinson and Company) and sealed with a plastic closure. The BD Phoenix™ ID/AST System is described in, e.g., U.S. Pat. Nos. 5,922,593, 6,096,272, 6,372,485, 6,849,422, and 7,115,384, the contents of which are hereby incorporated by reference in their entirety. Table 2 and Table 3 summarize the results for identification of gram-positive and gram-negative bacteria, respectively. The identification of the microorganisms was confirmed using standard biochemical methods. These results indicate that the methods described herein allow for the rapid isolation of intact/viable microorganism, across a panel of various microorganisms, without the need for subculturing.

TABLE 2

Gram-positive panel identified by BD Phoenix™ ID

| Organism | Strains Tested | Lysis Buffer #1 Correct IDs | Lysis Buffer #1 Percent (%) Correct IDs | Lysis Buffer #2 Correct IDs | Lysis Buffer #2 Percent (%) Correct IDs |
|---|---|---|---|---|---|
| E. faecalis | 2 | 2 | | 2 | |
| E. faecium | 2 | 2 | | 2 | |
| Subtotal Enterococci | 4 | 4 | 100 | 4 | 100 |
| S. aureus | 4 | 4 | | 4 | |
| S. epidermidis | 2 | 2 | | 2 | |
| S. haemolyticus | 1 | 1 | | 0 | |
| S. sciuri | 1 | 0 | | 1 | |
| Subtotal Staphylococci | 8 | 7 | 87.5 | 7 | 87.5 |
| S. pyogenes | 1 | 1 | | 1 | |
| S. agalactiae | 2 | 2 | | 2 | |
| S. pneumoniae | 3 | 1 | | 0 | |
| S mitis | 1 | 0 | | 0 | |
| S. salivarius | 1 | 1 | | 1 | |
| Subtotal Streptococci | 8 | 5 | 62.5 | 4 | 50 |
| Grand Total | 20 | 16 | 80 | 15 | 75 |

TABLE 3

Gram-negative panel identified by BD Phoenix™ ID

| Organism | Strains Tested | Lysis Buffer #1 Correct IDs | Lysis Buffer #1 Percent (%) Correct IDs | Lysis Buffer #2 Correct IDs | Lysis Buffer #2 Percent (%) Correct IDs |
|---|---|---|---|---|---|
| E. coli | 2 | 2 | | 2 | |
| K. pneumoniae | 2 | 2 | | 1 | |
| E. cloacae | 1 | 1 | | 1 | |
| E. aerogenes | 1 | 1 | | 1 | |
| P. mirabilis | 1 | 1 | | 1 | |
| S. marcescens | 1 | 1 | | 1 | |
| Subtotal Enterics | 8 | 8 | 100 | 8 | 100 |
| P. aeruginosa | 2 | 2 | | 2 | |
| A. baumannii | 1 | 1 | | 1 | |
| S. maltophilia | 1 | 1 | | 1 | |
| Subtotal Nonfermenters | 4 | 4 | 100 | 4 | 100 |
| Grand Total | 12 | 12 | 100 | 12 | 100 |

Example 3

Isolation of Viable Microorganism from a PBC Sample Using Two Different Lysis Buffers and Subsequent AST Testing A portion of the pelleted microorganism obtained in Example 2 was used to inoculate 4.5 ml of BD Phoenix™ ID broth (Becton, Dickinson and Company) to make a cell density equivalent of approximately 0.5 McFarland Standard. A portion of the inoculum was use to inoculate the AST portion of a BD Phoenix™ ID/AST panel (Becton, Dickinson and Company). The BD Phoenix™ ID/AST System is described in, e.g., U.S. Pat. Nos. 5,922,593, 6,096,272, 6,372,485, 6,849,422, and 7,115,384, the contents of which are hereby incorporated by reference in their entirety.

The antimicrobial susceptibility minimal inhibitory concentration (MIC) for a series of antibiotics was calculated for each of the isolated microbial pellets prepared in Example 2 ("Test Method"). The MIC results from the microbial pellets from Example 2 were compared to the MIC results from the same strains obtained from plated pure cultures ("Control"). This comparison indicates whether the Test Method provides substantially equivalent results to the Control Method, i.e., the rate of essential agreement (EA) between the Test Method and the Control Method. A dilution difference of 0 indicates exact agreement between the Test Method and the Control Method. A dilution difference of −1 or +1 indicates that the Test Method is considered within EA to the Control Method, i.e., within normal test variation. Dilution differences outside this range, such as for example −4, +4, −3, +3, −2 and +2, indicates the results are not within essential agreement for the antibiotic/microorganism tested. The methods and verification of AST results are further described in "Verification and Validation of Procedures in the Clinical Microbiology Laboratory", Cumitech 31, February 1997, ASM Press.

The results of the AST testing are detailed in Tables 4-9 below. Table 10 lists the full drug name for the abbreviated drug codes in Tables 4-9.

TABLE 4

Staphylococcus and Enterococcus test strains for AST testing with samples prepared with lysis buffer #2

| DRUG CODE | −3 | −2 | −1 | 0 | 1 | 2 | 4 | Grand Total | EA | % EA |
|---|---|---|---|---|---|---|---|---|---|---|
| AM | | 2 | 3 | 6 | 1 | | | 12 | 10 | 83.3 |
| CC | | | 1 | 11 | | | | 12 | 12 | 100.0 |
| DAP | | | 3 | 9 | | | | 12 | 12 | 100.0 |
| E | | 2 | 1 | 9 | | | | 12 | 10 | 83.3 |
| FM | | | | 11 | 1 | | | 12 | 12 | 100.0 |
| FOX | | | | 12 | | | | 12 | 12 | 100.0 |
| GM | 1 | | | 10 | 1 | | | 12 | 11 | 91.7 |
| GMS | | | 1 | 11 | | | | 12 | 12 | 100.0 |
| LZD | | | 2 | 10 | | | | 12 | 12 | 100.0 |
| MI | | | 1 | 10 | | | | 12 | 11 | 91.7 |
| MXF | | | | 11 | 1 | | | 12 | 12 | 100.0 |
| OX | 2 | | 4 | 5 | 1 | | | 12 | 10 | 83.3 |
| P | 1 | | | 11 | | | | 12 | 11 | 91.7 |
| RA | | | | 10 | 2 | | | 12 | 12 | 100.0 |
| STS | | | 1 | 11 | | | | 12 | 12 | 100.0 |
| SXT | 1 | | | 11 | | | | 12 | 11 | 91.7 |
| SYN | | 1 | 3 | 8 | | | | 12 | 11 | 91.7 |
| TE | | | 1 | 9 | | 1 | 1 | 12 | 10 | 83.3 |
| VA | | 3 | | 8 | 1 | | | 12 | 9 | 75.0 |
| Grand Total | 5 | 8 | 21 | 183 | 8 | 2 | 1 | 228 | 212 | 93.0 |

TABLE 5

Staphylococcus and Enterococcus test strains for AST testing with samples prepared with lysis buffer #1

| DRUG CODE | −3 | −2 | −1 | 0 | 1 | 2 | 4 | Grand Total | EA | % EA |
|---|---|---|---|---|---|---|---|---|---|---|
| AM | | 1 | 4 | 6 | 1 | | | 12 | 11 | 91.7 |
| CC | | | 1 | 11 | | | | 12 | 12 | 100.0 |
| DAP | | | 3 | 9 | | | | 12 | 12 | 100.0 |
| E | | 3 | | 9 | | | | 12 | 9 | 75.0 |
| FM | | | | 11 | 1 | | | 12 | 12 | 100.0 |
| FOX | | | | 12 | | | | 12 | 12 | 100.0 |

TABLE 5-continued

*Staphylococcus* and *Enterococcus* test strains for AST testing with samples prepared with lysis buffer #1

| DRUG CODE | −3 | −2 | −1 | 0 | 1 | 2 | 4 | Grand Total | EA | % EA |
|---|---|---|---|---|---|---|---|---|---|---|
| GM | 1 | | | 10 | 1 | | | 12 | 11 | 91.7 |
| GMS | | | 1 | 11 | | | | 12 | 12 | 100.0 |
| LZD | | | 3 | 9 | | | | 12 | 12 | 100.0 |
| MI | | | 2 | 9 | 1 | | | 12 | 11 | 91.7 |
| MXF | | | | 12 | | | | 12 | 12 | 100.0 |
| OX | 2 | | 4 | 5 | 1 | | | 12 | 10 | 83.3 |
| P | | | 1 | 11 | | | | 12 | 12 | 100.0 |
| RA | | | | 11 | 1 | | | 12 | 12 | 100.0 |
| STS | | | 1 | 11 | | | | 12 | 12 | 100.0 |
| SXT | | | | 12 | | | | 12 | 12 | 100.0 |
| SYN | | | 3 | 8 | 1 | | | 12 | 12 | 100.0 |
| TE | | | 1 | 8 | 1 | 1 | 1 | 12 | 10 | 83.3 |
| VA | | 3 | 1 | 7 | 1 | | | 12 | 9 | 75.0 |
| Grand Total | 3 | 7 | 25 | 182 | 8 | 2 | 1 | 228 | 215 | 94.3 |

TABLE 6

*Streptococcus* strains for AST testing with samples prepared with lysis buffer #2

| DRUG CODE | −3 | −2 | −1 | 0 | 1 | 2 | Grand Total | EA | % EA |
|---|---|---|---|---|---|---|---|---|---|
| AMX | | | 1 | 7 | | | 8 | 8 | 100.0 |
| C | | | | 8 | | | 8 | 8 | 100.0 |
| CC | | | | 8 | | | 8 | 8 | 100.0 |
| CTX | | | | 8 | | | 8 | 8 | 100.0 |
| E | | | | 8 | | | 8 | 8 | 100.0 |
| FEP | | | | 8 | | | 8 | 8 | 100.0 |
| LVX | | | | 6 | 1 | 1 | 8 | 7 | 87.5 |
| LZD | | | 1 | 7 | | | 8 | 8 | 100.0 |
| MEM | | | 1 | 6 | 1 | | 8 | 8 | 100.0 |
| MXF | | | | 7 | 1 | | 8 | 8 | 100.0 |
| P | 1 | 1 | 1 | 3 | 2 | | 8 | 6 | 75.0 |
| SXT | | | | 8 | | | 8 | 8 | 100.0 |
| SYN | | | | 8 | | | 8 | 8 | 100.0 |
| TE | | | | 8 | | | 8 | 8 | 100.0 |
| TEC | | | | 8 | | | 8 | 8 | 100.0 |
| TEL | | | | 7 | 1 | | 8 | 8 | 100.0 |
| VA | | | | 8 | | | 8 | 8 | 100.0 |
| Grand Total | 1 | 1 | 4 | 123 | 6 | 1 | 136 | 133 | 97.8 |

TABLE 7

*Streptococcus* strains for AST testing with samples prepared with lysis buffer #1

| DRUG CODE | −3 | −2 | −1 | 0 | 1 | Grand Total | EA | % EA |
|---|---|---|---|---|---|---|---|---|
| AMX | | | 1 | 6 | | 7 | 7 | 100.0 |
| C | | | | 6 | 1 | 7 | 7 | 100.0 |
| CC | | | | 7 | | 7 | 7 | 100.0 |
| CTX | | | | 7 | | 7 | 7 | 100.0 |
| E | | | | 7 | | 7 | 7 | 100.0 |
| FEP | | | | 6 | 1 | 7 | 7 | 100.0 |
| LVX | | | | 5 | 2 | 7 | 7 | 100.0 |
| LZD | | | 1 | 6 | | 7 | 7 | 100.0 |
| MEM | | | 1 | 6 | | 7 | 7 | 100.0 |
| MXF | | | | 6 | 1 | 7 | 7 | 100.0 |
| P | 1 | 1 | 2 | 3 | | 7 | 5 | 71.4 |
| SXT | | | | 7 | | 7 | 7 | 100.0 |
| SYN | | | | 5 | 2 | 7 | 7 | 100.0 |
| TE | | | | 7 | | 7 | 7 | 100.0 |
| TEC | | | | 7 | | 7 | 7 | 100.0 |

TABLE 7-continued

*Streptococcus* strains for AST testing with samples prepared with lysis buffer #1

| DRUG CODE | −3 | −2 | −1 | 0 | 1 | Grand Total | EA | % EA |
|---|---|---|---|---|---|---|---|---|
| TEL | | | | 7 | | 7 | 7 | 100.0 |
| VA | | | | 6 | 1 | 7 | 7 | 100.0 |
| Grand Total | 1 | 1 | 5 | 104 | 8 | 119 | 117 | 99.3 |

TABLE 8

Gram-negative strains for AST testing with samples prepared with lysis buffer #2

| DRUG CODE | −2 | −1 | 0 | 1 | 2 | 3 | Total | EA | % EA |
|---|---|---|---|---|---|---|---|---|---|
| AM | | | 11 | 1 | | | 12 | 12 | 100.0 |
| AMC | | | 11 | 1 | | | 12 | 12 | 100.0 |
| AN | | | 12 | | | | 12 | 12 | 100.0 |
| ATM | | | 12 | | | | 12 | 12 | 100.0 |
| CAZ | | 1 | 11 | | | | 12 | 12 | 100.0 |
| CIP | | 1 | 10 | 1 | | | 12 | 12 | 100.0 |
| CRO | | | 12 | | | | 12 | 12 | 100.0 |
| CTX | | | 12 | | | | 12 | 12 | 100.0 |
| CZ | | | 11 | 1 | | | 12 | 12 | 100.0 |
| ETP | | | 12 | | | | 12 | 12 | 100.0 |
| FEP | | | 11 | | 1 | | 12 | 11 | 91.7 |
| FM | | | 9 | 2 | 1 | | 12 | 11 | 91.7 |
| FOX | | | 11 | 1 | | | 12 | 12 | 100.0 |
| GM | | | 9 | 3 | | | 12 | 12 | 100.0 |
| IPM | 1 | 1 | 9 | 1 | | | 12 | 11 | 91.7 |
| LVX | | | 11 | 1 | | | 12 | 12 | 100.0 |
| MEM | | | 12 | | | | 12 | 12 | 100.0 |
| NN | | | 12 | | | | 12 | 12 | 100.0 |
| SXT | | | 12 | | | | 12 | 12 | 100.0 |
| TE | | | 12 | | | | 12 | 12 | 100.0 |
| TZP | | 1 | 9 | 1 | | 1 | 12 | 11 | 91.7 |
| Grand Total | 1 | 1 | 231 | 13 | 2 | 1 | 252 | 248 | 98.4 |

TABLE 9

Gram-negative strains for AST testing with samples prepared with lysis buffer #1

| DRUG CODE | −4 | −2 | −1 | 0 | 1 | 2 | Total | EA | % EA |
|---|---|---|---|---|---|---|---|---|---|
| AM | | | | 11 | 1 | | 12 | 12 | 100.0 |
| AMC | | | | 12 | | | 12 | 12 | 100.0 |
| AN | | | | 12 | | | 12 | 12 | 100.0 |
| ATM | | | | 12 | | | 12 | 12 | 100.0 |
| CAZ | | | | 12 | | | 12 | 12 | 100.0 |
| CIP | | | 1 | 10 | 1 | | 12 | 12 | 100.0 |
| CRO | | | 1 | 11 | | | 12 | 12 | 100.0 |
| CTX | | | | 12 | | | 12 | 12 | 100.0 |
| CZ | | | | 11 | 1 | | 12 | 12 | 100.0 |
| ETP | | | | 12 | | | 12 | 12 | 100.0 |
| FEP | | | 1 | 9 | 1 | 1 | 12 | 10 | 83.3 |
| FM | | | | 10 | 2 | | 12 | 12 | 100.0 |
| FOX | | | | 12 | | | 12 | 12 | 100.0 |
| GM | | | | 9 | 3 | | 12 | 12 | 100.0 |
| IPM | | 1 | 1 | 9 | 1 | | 12 | 11 | 91.7 |
| LVX | | | | 11 | 1 | | 12 | 12 | 100.0 |
| MEM | | 1 | | 11 | | | 12 | 11 | 91.7 |
| NN | | | | 12 | | | 12 | 12 | 100.0 |
| SXT | | | | 12 | | | 12 | 12 | 100.0 |

TABLE 9-continued

Gram-negative strains for AST testing with
samples prepared with lysis buffer #1

| DRUG CODE | -4 | -2 | -1 | 0 | 1 | 2 | Total | EA | % EA |
|---|---|---|---|---|---|---|---|---|---|
| TE |  |  |  | 12 |  |  | 12 | 12 | 100.0 |
| TZP |  |  | 1 | 9 | 2 |  | 12 | 12 | 100.0 |
| Grand Total | 1 | 2 | 4 | 231 | 13 | 1 | 252 | 248 | 98.4 |

TABLE 10

Antibiotics used in the AST Panels of Tables 4-9.

| Drug Code | Full Drug Name |
|---|---|
| AM | Ampicilin |
| AMC | Amoxicillin - Clavulanate |
| AMX | Amoxicillin |
| AN | Amikacin |
| ATM | Aztreonam |
| C | Chloramphenicol |
| CAZ | Ceftazidime |
| CC | Clindamycin |
| CIP | Ciprofloxacin |
| CRO | Ceftriaxone |
| CTX | Cefotaxime |
| CZ | Cefazolin |
| DAP | Daptomycin |
| E | Erythromycin |
| ETP | Ertapenem |
| FEP | Cefepime |
| FM | Nitrofurantoin |
| FOX | Cefoxitin |
| GM | Gentamicin |
| GMS | High-level Gentamicin |
| IPM | Imipenem |
| LVX | Levofloxacin |
| LZD | Linezolid |
| MEM | Meropenem |
| MI | Minocycline |
| MXF | Moxifloxacin |
| NN | Tobramycin |
| OX | Oxacillin |
| P | Penicillin |
| RA | Rifampin |
| STS | High-level streptomycin |
| SXT | Bactrim |
| SYN | Synercid |
| TE | Tetracycline |
| TEC | Teicoplanin |
| TEL | Telithromycin |
| TZP | Piperacillin - Tazobactam |
| VA | Vancomycin |

For the twelve (12) gram-positive microorganisms and nineteen (19) antibiotics tested, the EA rate was greater than 80% EA for 17/19 antibiotics, including 12/19 at 100% EA, i.e., exact agreement. For the eight (8) Streptococcus isolates and twelve (12) antibiotics, the EA rate was greater than 85% EA for 16/17 antibiotics, including 15/17 at 100% EA. For the twelve (12) gram-negative microorganisms and twenty-one (21) antibiotics tested, the EA rate was greater than 90% for 20/21 antibiotics, including 17/21 at 100% EA. The EA was similar for both lysis buffers for all AST results reported here.

These results illustrate that the addition of choline in methods utilizing lysis buffers to rapidly isolate viable microorganism(s) from a PBC sample can be used with a wide variety of organisms, including *S. pneumoniae*, while maintaining cell viability required for accurate AST testing. In addition, the high rates of AST agreement among both lysis buffers indicates that choline helps to mitigate the autolysis effect of various lysis buffers that often interferes with successful recovery of viable microorganism(s).

Example 4

Isolation and Identification of Various Streptococci Strains from a PBC Sample

PBC samples of four different Streptococci strains were prepared by seeding BD BACTEC™ blood culture bottles (Becton, Dickinson and Company) with each of the microorganisms, placing the sealed culture bottles in a BD BACTEC™ FX Automated Blood Culture Instrument (Becton, Dickinson and Company), and incubating the bottle until a positive result was indicated, usually within 12 to 24 hours. A portion of the PBC sample (5 ml) was treated with 0.5 ml of a 20% by volume aqueous solution of choline chloride or with 0.5 ml of de-ionized water as a control, and incubated at room temperature for 20 minutes. The final concentration of choline chloride, when combined with the sample, was 1.8% by volume. The PBC sample containing the choline chloride solution or de-ionized water was centrifuged at 160×g for 5 minutes. Lysis buffer #1 (5 ml), as described in Example 2, was added to the supernatant and incubated at room temperature for 5 minutes. The mixture was centrifuged at 2200×g for 10 minutes. The supernatant was discarded while the pellet, containing isolated microorganism, was retained for identification by MALDI-TOF MS. The pellet of the isolated microorganism was resuspended in 600 μl of de-ionized water or 2 mM OG in a microcentrifuge tube. The turbidity of the sample was visually adjusted to >0.5 McFarland Standard. Resuspended sample was spotted onto a MALDI-TOF MS plate and the sample was allowed to air dry. Formic acid (1 μl of a 70% by volume aqueous solution) was overlaid onto the sample and allowed to air dry. The dried sample was overlaid with 1 μl of MALDI matrix solution (MALDI matrix solution prepared by dissolving 2.5 mg of HCCA in 250 μl of 2.5% trifluoroacetic acid and 47.5% acetonitrile in de-ionized water) and allowed to air dry before identification by MALDI-MS. All mass spectrometry data was recorded on a Bruker Microflex LT with Biotyper 2.0 software.

The results are summarized in Table 11 below. The results indicate that the presence of a choline solution in the sample preparation buffer allows for the identification of range of Streptococci strains, including *S. pneumoniae*, which could not be identified in sample preparation methods that did not include a choline solution.

TABLE 11

Identification of *Streptococci* strains by MALDI-MS.

| Treatment | Resuspension | *S. pyrogenes* | *S. agalactiae* | *S. pneumoniae* | *S. pneumoniae* |
|---|---|---|---|---|---|
| Choline Chloride | Water | Correctly Identified | Correctly Identified | Correctly Identified | Correctly Identified |
| Choline Chloride | OG | Correctly Identified | Correctly Identified | Correctly Identified | Correctly Identified |
| Water | Water | Correctly Identified | Correctly Identified | Not Identified | Not Identified |
| Water | OG | Correctly Identified | Correctly Identified | Not Identified | Not Identified |

Although the invention herein has been described with reference to particular embodiments, it is to be understood that these embodiments are merely illustrative of the principles and applications described herein. It is therefore to be understood that numerous modifications may be made to the illustrative embodiments and that other arrangements may be devised without departing from the spirit and scope of the various embodiments described herein as defined by the appended claims.

The invention claimed is:

1. A method for isolating viable microorganism from a positive blood culture sample determined to contain at least one microorganism therein, comprising:
obtaining a positive blood culture sample determined to contain at least one viable microorganism;
incubating the sample with a choline-containing solution and a lysis buffer, wherein the lysis buffer lyses blood cells in the sample;
isolating the at least one viable microorganism from the remainder of the sample;
optionally, preparing a plated pure culture or an inoculum from the isolated viable microorganism; and
analyzing the isolated viable microorganism or optional plated pure culture or inoculum.

2. The method of claim 1, wherein the at least one microorganism is selected from the group consisting of gram-positive bacteria, gram-negative bacteria, and yeast.

3. The method of claim 1, wherein the at least one microorganism is $S.$ $pneumoniae$.

4. The method of claim 1, wherein the choline-containing solution comprises at least one quarternary ammonium salt containing a N,N,N-trimethylethanolammonium cation selected from the group consisting of the general formula:

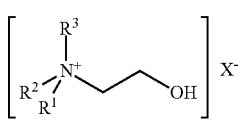

Formula 1 wherein $R_1$, $R^2$, and $R^3$ independently represent one selected from the group consisting of a saturated hydrocarbon group, an unsaturated hydrocarbon group, an aromatic group, and combinations thereof; and X represents a negative charged group.

5. The method of claim 4, wherein X is selected from the group consisting of chloride, fluoride, nitrate, and bicarbonate.

6. The method of claim 4, wherein the choline -containing solution comprises choline chloride.

7. The method of claim 4, wherein the choline -containing solution comprises phosphorylcholine.

8. The method of claim 1, wherein the final concentration of choline when incubated with the sample is greater than or equal to about 0.25% by volume.

9. The method of claim 8, wherein the final concentration of choline when incubated with the sample is greater than or equal to about 1% by volume.

10. The method of claim 8, wherein the concentration of choline in the sample during incubation is about 1.8% by volume.

11. The method of claim 8, wherein the concentration of choline in the sample during incubation is about 4% by volume.

12. The method of claim 8, wherein the concentration of choline in the sample during incubation is in the range of about 0.25% by volume to about 10% by volume.

13. The method of claim 8, wherein the concentration of choline in the sample during incubation is in the range of about 1% by volume to about 5% by volume.

14. The method of claim 1, wherein the lysis buffer comprises at least one detergent selected from the group consisting of octyl-B-D-glucopyranoside, n-nonyl β-D-glucoside, octanoyl-N-methylglucamide, nonanoyl-N-methylglucamide, decanoyl-N-methylglucamide, n-dodecyl-β-D-maltoside, n-octyl-rac-2,3-dioxypropylsulfoxide, Triton X-100, saponin, and combinations thereof.

15. The method of claim 1, wherein the duration of the incubating step is up to 20 minutes and the temperature of the incubation is room temperature.

16. A method for isolating viable microorganism from a positive blood culture sample determined to contain at least one microorganism therein, comprising:
obtaining a positive blood culture sample determined to contain at least one viable microorganism;
combining the sample with a choline-containing solution;
incubating the sample combined with the choline-containing solution;
centrifuging the sample combined with the choline-containing solution at a low speed to produce a pellet and a supernatant;
discarding the pellet while retaining the supernatant;
adding a lysis buffer to the supernatant, wherein the lysis buffer lyses blood cells in the sample;
incubating the supernatant with the lysis buffer;
centrifuging the supernatant with the lysis buffer at a high speed to produce a second pellet and a second supernatant;
discarding the second supernatant while retaining the second pellet containing isolated viable microorganism; and
analyzing the isolated viable microorganism.

17. The method of claim 16, wherein the at least one microorganism is selected from the group consisting of gram-positive bacteria, gram-negative bacteria, and yeast.

18. The method of claim 16, wherein the at least one microorganism is $S.$ $pneumoniae$.

19. The method of claim 16, wherein the choline-containing solution comprises at least one quarternary ammonium salt containing a N,N,N-trimethylethanolammonium cation selected from the group consisting of the general formula:

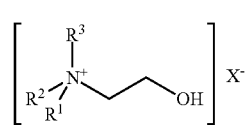

Formula 1 wherein $R_1$, $R^2$, and $R^3$ independently represent one selected from the group consisting of a saturated hydrocarbon group, an unsaturated hydrocarbon group, an aromatic group, and combinations thereof; and X represents a negative charged group.

20. The method of claim 19, wherein X is selected from the group consisting of chloride, fluoride, nitrate, and bicarbonate.

21. The method of claim 19, wherein the choline -containing solution comprises choline chloride.

22. The method of claim 16, further comprising preparing a plated pure culture from the isolated microorganism and analyzing the microorganism obtained from the plated pure culture.

23. The method of claim 16, further comprising preparing an inoculum from the isolated microorganism and analyzing the microorganism obtained from the inoculum.

24. A method for isolating viable microorganism from a positive blood culture sample determined to contain at least one microorganism therein, comprising:
obtaining a positive blood culture sample determined to contain at least one viable microorganism;
incubating the sample with a choline-containing solution and a lysis buffer simultaneously, wherein the lysis buffer lyses blood cells in the sample;
centrifuging the sample with the choline-containing solution and the lysis buffer at a high speed to produce a pellet and a supernatant;
discarding the supernatant while retaining the pellet containing isolated viable microorganism;
analyzing the isolated viable microorganism or optional plated pure culture or inoculum.

25. The method of claim 24, wherein the at least one microorganism is selected from the group consisting of gram-positive bacteria, gram-negative bacteria, and yeast.

26. The method of claim 24, wherein the at least one microorganism is *S. pneumoniae*.

27. The method of claim 24, wherein the choline-containing solution comprises at least one quarternary ammonium salt containing a N,N,N-trimethylethanolammonium cation selected from the group consisting of the general formula:

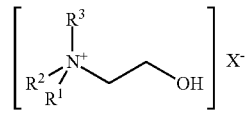

Formula 1 wherein $R_1$, $R^2$, and $R^3$ independently represent one selected from the group consisting of a saturated hydrocarbon group, an unsaturated hydrocarbon group, an aromatic group, and combinations thereof; and X represents a negative charged group.

28. The method of claim 27, wherein X is selected from the group consisting of chloride, fluoride, nitrate, and bicarbonate.

29. The method of claim 27, wherein the choline-containing solution comprises choline chloride.

30. The method of claim 24, further comprising preparing a plated pure culture from the isolated microorganism and analyzing the microorganism obtained from the plated pure culture.

31. The method of claim 24, further comprising preparing an inoculum from the isolated microorganism and analyzing the microorganism obtained from the inoculum.

* * * * *

UNITED STATES PATENT AND TRADEMARK OFFICE
CERTIFICATE OF CORRECTION

PATENT NO. : 8,603,769 B2
APPLICATION NO. : 13/647072
DATED : December 10, 2013
INVENTOR(S) : Liping Feng et al.

It is certified that error appears in the above-identified patent and that said Letters Patent is hereby corrected as shown below:

In the claims

Column 18, line 11, delete "$R_1$" and insert therefor -- $R^1$ --.

Signed and Sealed this
Twenty-second Day of December, 2015

Michelle K. Lee
*Director of the United States Patent and Trademark Office*